United States Patent [19]

Herrmann et al.

[11] Patent Number: 5,728,839
[45] Date of Patent: Mar. 17, 1998

[54] METAL COMPLEXES WITH HETEROCYCLES CARBENES

[75] Inventors: Wolfgang A. Herrmann, Freising; Martina Elison, Munich; Jakob Fischer, Kirchdorf; Christian Kocher, Munich; Karl Ofele, Puchheim, all of Germany

[73] Assignee: Hoechst Aktiengesellschaft, Germany

[21] Appl. No.: 581,029

[22] Filed: Dec. 29, 1995

[30] Foreign Application Priority Data

Dec. 29, 1994 [DE] Germany ............... 44 47 066.5

[51] Int. Cl.$^6$ .................. C07F 7/02; C07F 15/00
[52] U.S. Cl. ............. 548/103; 548/110; 548/311.7; 548/312.4; 548/312.7; 548/313.7; 548/347.1; 548/348.1; 548/379.1; 548/379.4
[58] Field of Search ............ 548/103, 110, 548/311.7, 312.4, 312.7, 313.7, 347.1, 348.1, 379.1, 379.4

[56] References Cited

PUBLICATIONS

Journal of Organometallic Chem., 481, 1994, 89–95 Cetinkaya et al.
Journ. of Amer. Chem. Soc., 1994, 116, 4391–4394, Arduengo et al.
Homoleptische Carbenkomplexe article, Fehlhammer et al, 79–89.
Thermal Dehydrochlorination . . . , Demidov, et al 1988, 652–654.
Tetrahedron Letters No. 18, pp. 1535–1538, 1978, Ito et al.
Journ. Organo Metallic Chemistry, pp.19–26, 1994, Alonso et al.
Journal of Organo Metallic Chem., vol. 484, Nos. 1–2, 245–257, 1992.
Angewandte Chemie, Herrmann et al, 1995, No. 21, 2371–2374.
CA90:23223x A New Preparation . . . Complexes. Ito et al., p. 671, 1979.
CA97:92533e Reactivity . . . Redox Behavior. Tweedle et al., 1982.
CA116:214672 Hemoleptic Carbene Complexes. IV. Tetrakis . . . —Platinum. Fehlhammer et al., 1992.
CA120:323832p Low–Coordinate . . . Platinum (0), Arduengo et al., 1994.
CA123:112333a Homoleptic . . . Route. Fehlhammer et al, 1995.

*Primary Examiner*—Joseph McKane
*Attorney, Agent, or Firm*—Bierman, Muserlian & Lucas

[57] ABSTRACT

A complex of the formula $$[L_a M_b X_c]^r (A)_n \qquad I$$

as described in the application useful as homogenous catalysts.

12 Claims, 3 Drawing Sheets

METAL COMPLEXES WITH HETEROCYCLES CARBENES

Complexes of a transition metal as central atom and control ligands bound thereto have recently found frequent application as homogenous catalysts. They are particularly important for reactions leading to the construction of CC, CH, NC and OC bonds. Examples of industrial processes carried out in the presence of such catalysts are the hydrogenation and hydroformylation of CC-unsaturated organic compounds, preferably of olefins. The control ligands used, which, usually employed in excess, also stabilize the complexes and, next to the central atom, determine the specific catalytic activity, have in the past been almost exclusively organic amines, phosphines or phosphites. The best known examples are complexes of the general formula $ClRhL_3$, which act as hydrogenation catalysts, and $H(CO)RhL_3$, which act as hydroformylation catalysts, L being triphenylphosphine in both cases.

Organic phosphines are useful as control ligands in industrial practice because of their variety, their catalytic activity and their selectively. Nonetheless, there are a number of disadvantages preventing their more widespread use. Chief among these is the oxidation sensitivity, which arises in particular in the presence of metals and metal ions. When catalysts based on phosphine complexes are used, it is therefore necessary to take measures to exclude oxidizing agents, such as oxygen or air, in order to reduce the losses of ligands, which are frequently costly to make. A further property which is common to all organic phosphines and limits their possible use is the irreversible cleavage of phosphorus-carbon bonds, which, for example in a hydroformylation, occurs to an increased extent above certain temperatures, depending on the type of phosphine, and leads to the deactivation of the catalyst and thus to an uneconomically high phosphine consumption. Finally, the traditional alkyl- and arylphosphines, as well as the organic phosphites of the general formula $P(OR)_3$ (where R is alkyl or aryl) which are likewise used as ligands, do not make it possible to cover the entire range of electronic control of the catalytically active metal centers. More particularly, there is a want of strongly nucleophilic, i.e. electron-rich, ligands which are resistant to oxidizing agents and enter a stable bond with the metal. In principle, organic amines would be suitable for this purpose, but these ligands too are oxidation-sensitive and not usable for the CH and CC linking reactions mentioned.

OBJECTS OF THE INVENTION

It is an object of the invention to provide novel metal complexes free of the above disadvantages and which are easy to synthesize in an inexpensive manner.

It is another object of the invention to vary the control ligands in a simple manner to prepare metal complexes to solve individual catalytic problems.

These and other objects and advantages of the invention will become obvious from the following detailed description.

THE INVENTION

The novel complexes of the invention have the formula

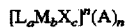   I wherein M is ion of oxidation state of 1 to 8 of metals of groups 8, 9 and 10 of the periodic table as central atom, X is uni- or multidentate charged or uncharged ligands bound to the central atom, and L are ligands similarly bound to the central atom M, comprising monocarbenes of the formulae

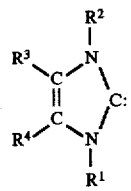   II and

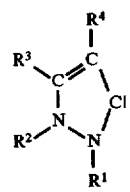   III or dicarbenes of the formulae

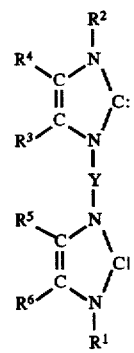   IV and

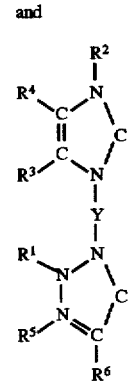   V wherein $R^1$, $R^2$, $R^3$, $R^4$, $R^5$ and $R^6$ are individually selected from the group consisting of optionally sulfonated alkyl of 1 to 7 carbon atoms, optionally sulfonated aliphatic mono- or polycyclics of 5 to 18 carbon atoms, optionally sulfonated alkenyl of 2 to 5 carbon atoms, optionally sulfonated aryl of 6 to 14 carbon atoms and optionally sulfonated arylalkyl of 7 to 19 carbon atoms, $R^3$, $R^4$, $R^5$ and $R^6$ also can be hydrogen, $R^3$ and $R^4$ together and $R^5$ and $R^6$ together in each case with the carbon atoms to which they are attached individually form fused and optionally sulfonated groups of 3 to 7 carbon atoms, Y is an optionally unsaturated alkylidene of 1 to 4 carbon atoms or a dialkylsilylene or a tetraalkyldisilylene, A is a singly charged anion or the chemical equivalent of a multiply charged anion, b is an integer from 1 to 3, a is an integer from 1 to 5×b and c=0 or an integer from 1 to 4×b, n=0 or an integer from 1 to 6, and c+n>0, but not (N, N'-dimethylbenzimidazolin-2-ylidene)-chloro-(1,5-cyclooctadiene)-rhodium .

The novel complexes are of elements of groups 8, 9 and 10 of the periodic table (corresponding to the IUPAC recommendation of 1985). The common feature of these complexes is the presence of heterocyclic carbene ligands with or without other ligands. The complexes dissolve in organic solvents and/or water without decomposing. Optionally, $R^1$, $R^2$, $R^3$, $R^4$, $R^5$ and $R^6$ can be identical or different sulfonated, substituted, chiral and/or polymer-immobilized alkyl radicals of 1-7 carbon atoms.

Complexes of metals of groups 8, 9 and 10 of the periodic table with carbenes derived from imidazole or pyrazole and derivatives thereof and in which the metal is present in an oxidation state of +1 to +8, excluding the recently described compound (N,N-dimethylbenzimidazolin-2-ylidene)-chloro-(1,5-cyclooctadiene)-rhodium (cf. J. Organometall. Chem. Vol. 481, (1994), pgs. 89 to 95), have not been disclosed before.

The novel compounds are soluble in organic solvents and also water, particularly if they contain sulfonate-substituted, aliphatic or aromatic groups. They are notable for appreciable thermal stability, in some instances to above 350° C., high oxidation stability and pronounced catalytic activity in reactions which lead to the construction of carbon-carbon, carbon-hydrogen and carbon-silicon bonds. The novel compounds, unlike phosphine and phosphite complexes, have no tendency to dissociate, so that there is no need for excess ligand to control the reactivity and to stabilize the complex. This characteristic of the claimed carbene-metal complexes was unforeseeable, since complexes with carbene ligands are known for use as catalysts for olefin and alkyne metathesis, i.e. a reaction where molecules with carbon-carbon multiple bonds are cleaved, with decisive involvement of the carbene ligand.

The novel complexes are derived from the metals iron, ruthenium, osmium, cobalt, rhodium, iridium, nickel, palladium and platinum. Uni- or multidentate ligands which can be present in the complexes as well as the carbenes and are represented by X in formula I are hydrogen, hydrogen ion, halogens, halogen ions, pseudohalides, carboxylate ions, sulfonate ions, amide groups, alcoholate groups, acetylacetonate, carbon monoxide, alkyls of 1 to 7 carbon atoms, nitrogen monoxide, nitriles, isonitriles, mono- or diolefins, alkynes and π-aromatic groups. If a plurality of these ligands are present in the molecule of the complex, they can be identical or different.

In the mono- or dicarbenes derived from imidazole and from pyrazole or derivatives thereof, conforming to formulae II, III, IV and V, $R^1$ to $R^6$ are each preferably methyl, isopropyl, tert-butyl, benzyl, triphenylmethyl, phenyl, tolyl, xylyl, mesityl or adamantyl, $R^1$ and $R^2$ are each more preferably methyl, tert-butyl, phenyl, benzyl or o-tolyl, and $R^3$ and $R^4$ are each more preferably hydrogen or methyl.

$R^3$ and $R^4$ and $R^5$ and $R^6$ can be combined with two adjacent carbon atoms of the imidazole ring or of the C-N grouping in the pyrazole ring to form a ring system. $R^3$ and $R^4$ on the one hand and $R^5$ and $R^6$ on the other are preferably $(CH)_4$, which leads to the formation of fused aromatic 6-ring, $(CH)_4$ and $(CH_2)_5$.

The Y bridge members of the dicarbenes of formulae IV and V are preferably methylene, dimethylmethylene, diphenylmethylene, 1,3-phenylene or ethylidene. Of the silicon-containing bridge members, dimethylsilylene and tetramethyldisilylene groups are preferred a is preferably 1 or 2, b is preferably 1; n is in particular from 0 to 3.

A is preferably halide, pseudohalide, tetraphenylborate, tetrafluoroborate, hexafluorophosphate, carboxylate, especially acetate, or a metal complex anion such as tetracarbonylcobaltate, hexafluoroferrate (III), tetrachloroferrate (III), tetrachloroaluminate or tetrachloropalladate (II).

The claimed complexes are obtainable in various ways. One method is to start from simple compounds, i.e. salts or metal complexes such as the acetylacetonates, metal carbonylates of each element which forms the central atom of the complex. Another method provides the novel compounds from complexes through ligand exchange or through elimination and/or substitution reactions, for example from common solvent complexes of these metal compounds such as $PdCl_2 \cdot (C_6H_5C\equiv N)_2$, $NiBr_2 \times 2$ DMF (DMF= dimethylformamide) or $Cl_2Pt[(CH_3)_2NCH_2CH_2N(CH_3)_2]$. The claimed compounds are also formed by simple addition of the carbene to the respective metal component, which addition may also involve breaking up a bridge structure.

Depending on their stability, the carbenes are either used in free form as in solution or, more frequently, prepared in a reaction mixture from compounds which can be converted into carbenes under the reaction conditions. The most important method of formation is the deprotonation of imidazolium or pyrazolium salts, optionally through the addition of bases such as metal hydrides, carbonyl metallates, metal carboxylates, metal alkoxides or metalamides.

The reaction of the starting materials, i.e. of the simple salts or complexes, with the carbenes and optionally further ligands is carried out by mixing the reactants in a solvent at room temperature or elevated temperatures. The reaction proceeds at a high rate and will in many cases be essentially over after a few minutes. However, to ensure completion of the reaction, it is advisable to observe reaction times of up to several hours, particularly when the starting materials are only in partial solution in the medium used, i.e. react from a suspension.

To prepare complexes with sulfonated ligands, which are soluble in water, at least one of the reactants has a sulfonated molecule or moiety.

An advantageous way of isolating the novel complexes from the reaction medium is to remove the solvent in a high vacuum. To purify the crude product, it is washed and crystallized from a suitable solvent or solvent mixture, determined in each case by preliminary experiments.

BRIEF DESCRIPTION OF DRAWINGS

The 3 sheets filed herewith illustrate the structural formulae of the complexes of Examples 1, 2 and 3.

In the following examples, there are described several preferred embodiments to illustrate the invention. However, it should be understood that the invention is not intended to be limited to the specific embodiments.

Figure 1:
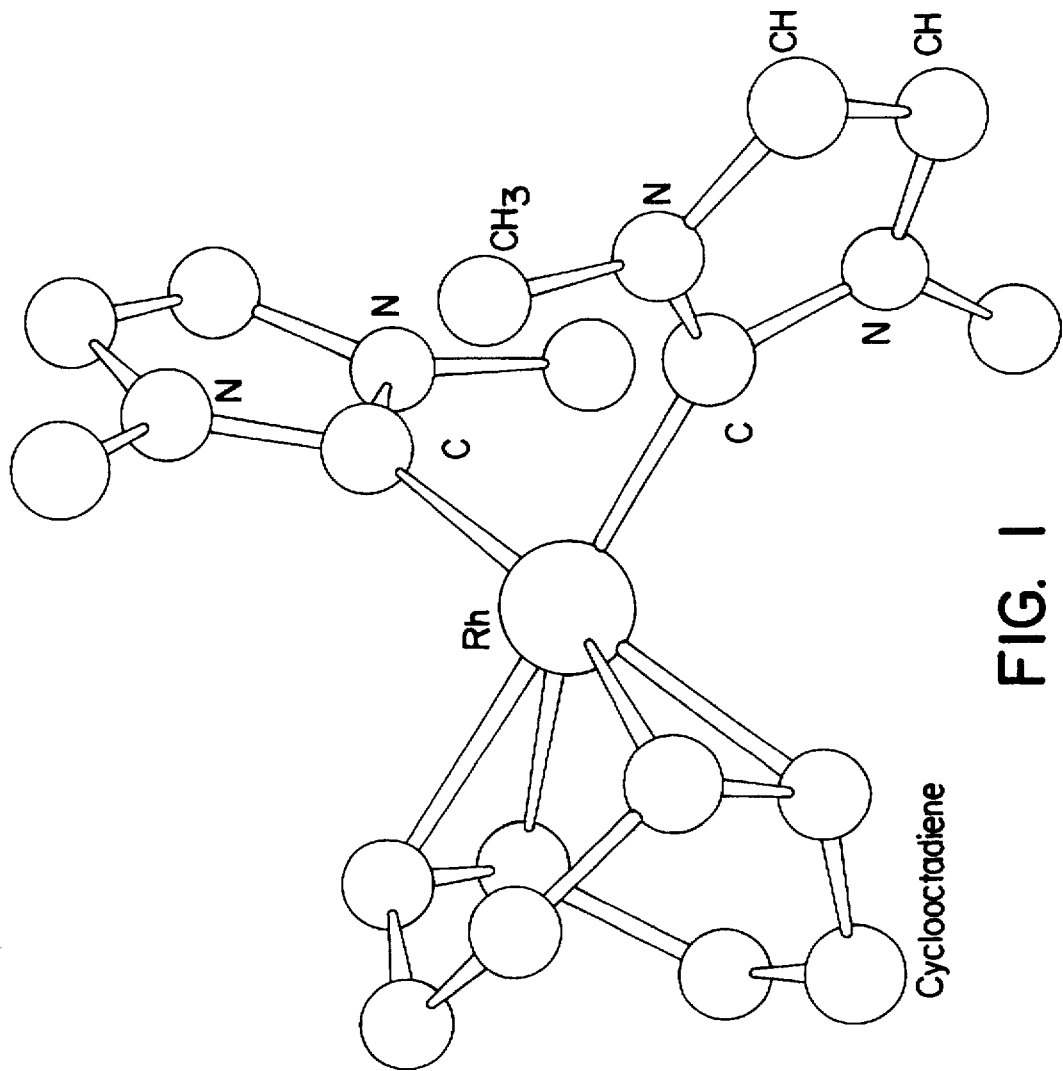
Figure 2:
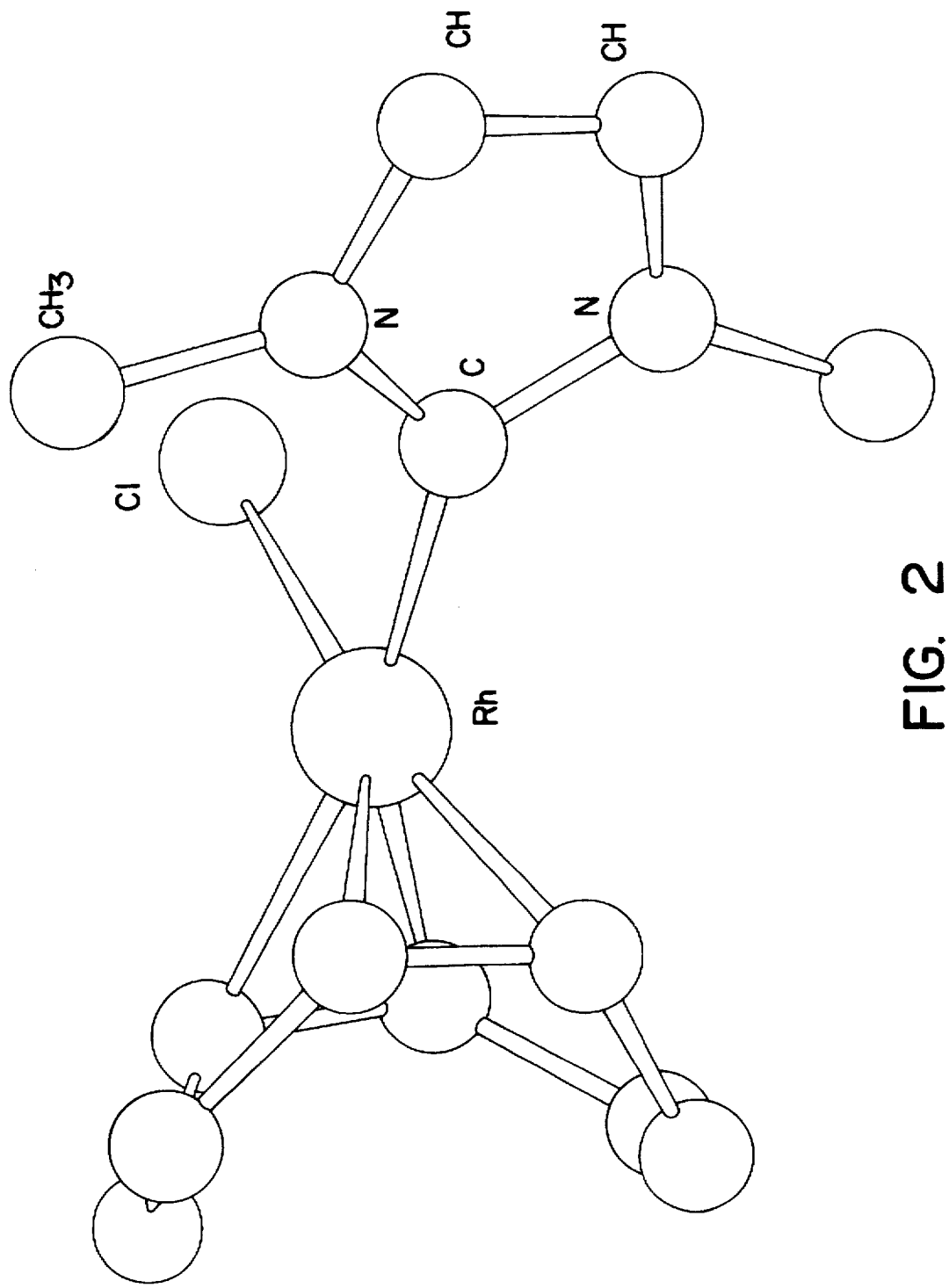
Figure 3:
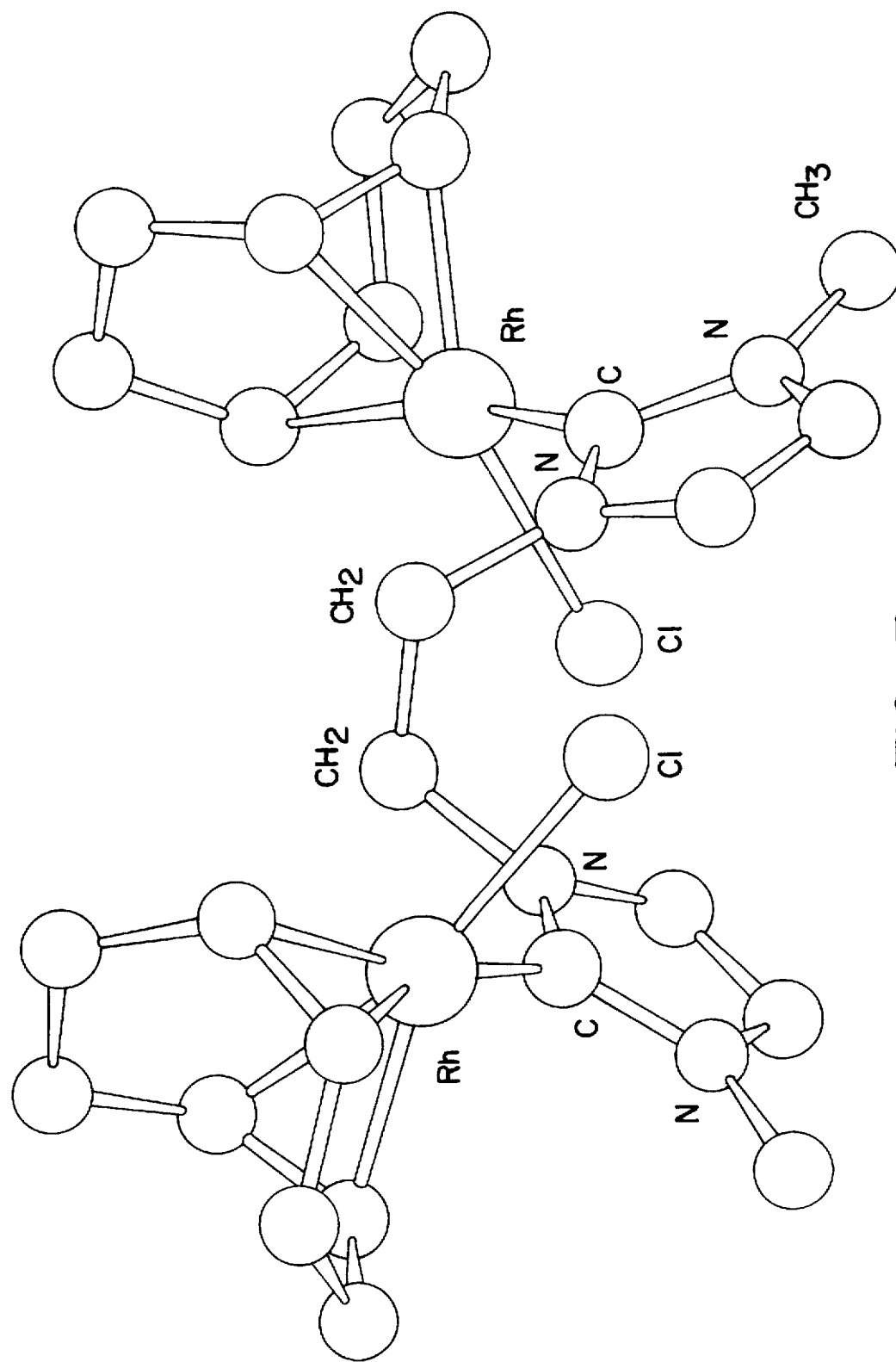

All reactions with organometallic compounds were carried out, unless otherwise stated, under the exclusion of atmospheric oxygen and moisture in standardized glass apparatus under an inert gas atmosphere (Schlenck tube technique). The nitrogen used as inert gas was purified and dried over copper oxide catalyst, silica gel and molecular sieve (4 Å). The solvents used were dried by a standard method and stored over a molecular sieve (4 Å).

EXAMPLE 1

Chloro (η4-1,5-cyclooctadiene)-(1,3-dimethylimidazolin-2-ylidene)-rhodium (I)

1a) Preparation of 1,3-dimethylimidazolin-2-ylidene 8.69 g (38.8 mmol) of 1,3-dimethylimidazolium iodide were dissolved with 1.03 g (42.7 mmol) of sodium hydride and 0.2 g (1.8 mmol) of potassium tert-butoxide in 50 ml of tetrahydrofuran (THF) and stirred for 4 hours at room temperature in a Schlenck tube with an attached paraffin oil check valve. The solution turned yellow as a result of the free carbene being formed. The solvent was striped off in a high vacuum and the residue was distilled under reduced pressure in a microdistillation apparatus to obtain 1,3-dimethylimidazolin-2-ylidene in the form of a yellow oil. The carbene was dissolved at once in 60 ml of THF and stored at −30° C.

1b) Preparation of chloro-($\eta^4$-1,5-cyclooctadiene)-(1,3-dimethylimidazolin-2-ylidene)-rhodium (I)

247 mg (0.5 mmol) of di($\mu$-chloro)-bis-($\eta^4$-1,5-cyclooctadiene)-dirhodium were taken up at room temperature in 20 ml of absolute THF and admixed with 192 mg (1 mmol) of 1,3-dimethylimidazolin-2-ylidene. The immediate reaction was evident from a change in the color from pale yellow to deep yellow. Stirring was continued at room temperature for a further 15 minutes and then the solvent was stripped off in a high vacuum. The residue was purified by washing with 10 ml of diethyl ether. The product was taken up in 10 ml of methylene chloride and carefully covered with 30 ml of pentane. The resulting yellow crystals were freed of the solvent mixture by decanting and dried in a high vacuum. The compound dissolved very readily in chloroform and methylene chloride, readily in THF and toluene, sparingly in diethyl ether and pentane with a yellow color. It did not decompose on prolonged heating in moist toluene in an oxygen atmosphere. The yield was 310 mg (91%) of the desired product.

Characterization

Analysis (calculated for $C_{13}H_{20}ClN_2Rh$)

| | | | |
|---|---|---|---|
| calculated | % C 45.57 | % H 5.88 | % N 8.17 |
| observed | C 45.63 | H 5.98 | N 8.35 |

$^1$H-NMR (400 MHz, CDCl$_3$, 20° C., ppm) 6.8 (s, 2H) and 4.1 (s, 6H) carbene 5.0 (2H), 3.3 (2H), 2.4 (4H), 1.9 (4H) cyclooctadiene $^{13}$C{$^1$H}-NMR 182.6 d, carbene carbon atom $^1$J(C-Rh)= 20 Hz 121.9 and 37.6 carbene 98.5, 67.7, 33.0, 28.9 cyclooctadiene IR (KBr) $\nu$ in cm$^{-1}$ 3500, 3154, 3103, 2931, 2875, 2828, 1652, 1507, 1456, 1378, 1328, 1228, 1115, 1079, 992, 957, 865, 816, 744, 694, 459

Structure

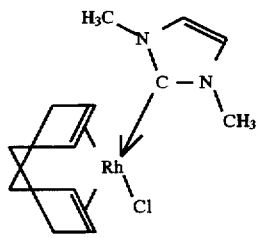

EXAMPLE 2

[($\eta^4$-1,5-cyclooctadiene)-bis-(1,3-dimethylimidazolin-2-ylidene)-rhodium(I)]-chloride 247 mg (0.5 mmol) of di($\mu$-chloro)bis($\eta^4$-1,5-cyclooctadiene)-dirhodium were taken up at room temperature in 20 ml of absolute THF and admixed with 279 mg (3 mmol) of 1,3-dimethylimidazolin-2-ylidene. The immediate reaction was evident from a change in the color from pale yellow to deep yellow. Stirring was continued at room temperature for a further 3 hours and the solvent was stripped off in a high vacuum. The residue was purified by washing with 30 ml of diethyl ether after which the product was taken up in 10 ml of methylene chloride and carefully covered with 10 ml of pentane. The resulting yellow crystals were freed of the solvent mixture by decanting and drying in a high vacuum. The compound dissolved readily in chloroform and methylene chloride, moderately well in THF, water and toluene, and did not dissolve in diethyl ether and pentane. The yield was 410 mg (93%) of the desired product.

Characterization

Analysis (calculated for $C_{18}H_{28}ClN_4Rh$)

| | | | |
|---|---|---|---|
| calculated | % C 49.29 | % H 6.43 | % N 12.77 |
| observed | C 50.26 | H 6.44 | N 12.66 |

$^1$H-NMR (400 MHz, CDCl$_3$, 20° C., ppm) 7.0 (s, 4H) and 4.0 (s, 12H) carbene 4.2 (m, 4H), 2.3 (4H), 2.1 (4H) cyclooctadiene (COD)

$^{13}$C{$^1$H}-NMR 180.5 (d, J(C-Rh)=20 Hz) 123.1, 38.3 carbene 88.8 and 30.4 COD IR (KBr) $\nu$ in cm$^{-1}$ 3450, 3154, 3094, 2920, 2977, 2828, 1634, 1574, 1458, 1380, 1230, 1115, 1084, 991, 823, 744, 695, 668, 461

The metal complex was characterized by single-crystal X-ray structure analysis.

Structure

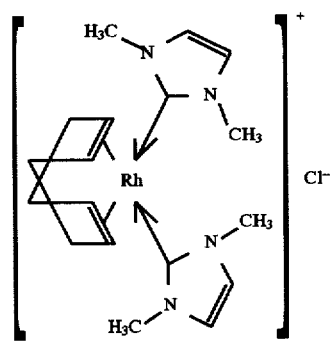

EXAMPLE 3

[1,2-bis-(3-methylimidazolin-2-ylidene)-ethylene]-bis-[chloro-($\eta^4$-1,5-cyclooctadiene)-rhodium (I)]

3a) Preparation of the ligand: 1,2-bis-(3-dimethylimidazolin-2-ylidene)-ethylene 352 mg (1 mmol) of 1,2-bis-(3-methylimidazolium-bromide)-ethylene were added together with 224 mg (2 mmol) of potassium tert-butoxide in 20 ml of absolute THF at −20° C. The reaction solution immediately turned yellow and the reaction solution containing the free dicarbene was further reacted in 3b).

3b) Preparation of [1,2-bis-(3-methylimidazolin-2-ylidene)-ethylene]bis[chloro($\eta^4$-1,5-cyclooctadiene)-rhodium (I)]

247 mg (0.5 mmol) of di($\mu$-chloro)-bis(-$\eta^4$-1,5-cyclooctadiene)-dirhodium were taken up at room temperature in 20 ml of absolute THF and admixed with 190 mg (1 mmol) of 1,2-bis-(3-methylimidazolin-2-ylidene)-ethylene (prepared in 3a). The immediate reaction was evident from a change in the color from pale yellow to deep yellow and stirring was continued at room temperature for a further 3 hours. The solvent was stripped off in a high vacuum, and the residue was purified by washing with 10 ml of diethyl ether. The product was taken up in 10 ml of methylene chloride and carefully covered with 20 ml of pentane. The resulting yellow crystals were freed of the solvent mixture by decanting and drying in high vacuum. The compound dissolved very readily in chloroform and methylene chloride. The yield was 80 mg (18%) of the desired product.

Characterization $^1$H-NMR (400 MHz, CDCl$_3$, 20° C., ppm) 6.85 (d, 2H, J=1.9 Hz), 6.47 (d, 2H, J=1.9 Hz) (imidazole) 4.01 (s, 6H) (N-methyl) 4.73 (m, 4H) (CH$_2$-CH$_2$) 3.34 (m, 4H), 3.22 (m, 4H), 2.44 (m, 4H), 2.00 (m, 4H) (COD) 5.17 (m, 4H), 4.98 (m, 4H) (olefinic COD protons)

$^{13}$C {$^1$H}-NMR 181.30 (d, $^1$J(C-Rh)=50.5 Hz) (carbene carbon atom) 123.85, 120.62 (imidazole) 37.76 (N-methyl) 50.85 (CH$_2$-CH$_2$) 69.18 (d, $^1$J(C-Rh)=14.6 Hz), 67.75 (d, $^1$J(C-Rh)=14.5 Hz) (olefinic carbon atoms COD) 29.45, 28.39 (COD)

The metal complex was characterized by single-crystal X-ray structure analysis.

Structure

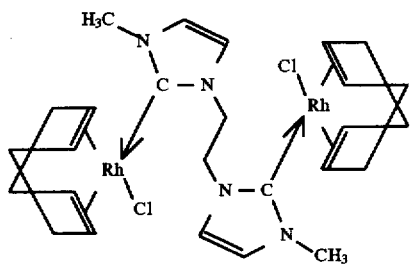

EXAMPLE 4

Dicarbonylchloro(1,3-dimethylimidazolin-2-ylidene)-rhodium (I)

200 mg (0.58 mmol) of chloro($\eta^4$-1,5-cyclooctadiene)-(1,3-dimethylimidazolin-2-ylidene)rhodium (I) were dissolved in 30 ml of absolute methylene chloride and the solution was then gassed with carbon monoxide for 10 minutes. After the solution had cleared, stirring was continued at room temperature for a further 15 minutes. The solvent was stripped off in a high vacuum, and the residue was purified by washing with 10 ml of diethyl ether. The product was taken up in 10 ml of methylene chloride and carefully covered with 30 ml of pentane. The resulting pale yellow crystals were freed of the solvent mixture by decanting and drying in a high vacuum. The compound dissolved very readily in chloroform and methylene chloride, readily in THF and toluene, sparingly in diethyl ether and pentane with a yellow color. The yield was 160 mg (95%) of the desired product.

Characterization

Analysis (calculated for C$_7$H$_8$ClN$_2$O$_2$Rh)

| calculated | % C 28.94 | % H 2.78 | % N 9.64 |
|---|---|---|---|
| observed | C 29.18 | H 2.86 | N 9.56 |

$^1$H-NMR (400 MHz, CDCl$_3$, 20° C., ppm) 3.87 (s, 6H, NCH$_3$), 6.93 (s, 2H, NCH)

$^{13}$C{$^1$H}-NMR (CDCl$_3$, 100.1 MHz, 20° C. 38.27 (NCH$_3$), 122.75 (NCH), 185.30 (d, $^1$J(CRh)=53 Hz, carbene carbon).

IR (KBr [cm$^{-1}$]) 2076 (s, ν(CO)), 2006 (sst, ν(CO))

MS (chemical ionization): m/z 290 (molecular peak, correct isotope pattern) 262 (M- CO, correct isotope pattern) 234 (262 - CO, correct isotope pattern) 199 (234 - Cl)

Structure

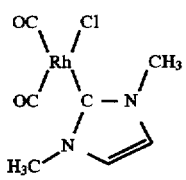

EXAMPLE 5

[$\eta^4$-1,5-cyclootadiene)bis(1,3-dimethylimidazolin-2-ylidene-rhodium (I)]-acetate 150 mg (0.277 mmol) of di(μ-chloro)bis($\eta^4$-1,5-cyclooctadiene)-dirhodium (I) were taken up at room temperature in 10 ml of absolute THF and admixed with 1.2 mmol of 1,3-dimethylimidazolin-2-ylidene. The originally yellow solution immediately threw a yellow precipitate and stirring was continued at room temperature for a further 10 minutes. The solvent was stripped off in a high vacuum, and the residue was purified by washing with 30 ml each of diethyl ether and pentane. The product was crystallized from methylene chloride by careful covering with pentane to obtain 101 mg (79%) of the desired product.

Characterization $^1$H-NMR (400 MHz, CDCl$_3$, 20° C.) 6.96 (s, 4H, olefinic carbene CH) 4.07 (m, olefinic COD-CH), 3.85 (s, 12H, N-Me), 2.28 (m, 8H COD-CH$_2$), 2.03 (s, 3H, Ac)

$^{13}$ C{$^1$H}-NMR (CDCl$_3$, 100.1 MHz, 20° C.) 180.3 (d, $^1$J(C-Rh)=50.0 Hz, carbene C), 176.5 (s, CH$_3$COO), 123.1 (s, olefinic carbene CH), 88.7 (s, olefinic COD-CH), 38.8 (s, N-CH$_3$), 30.5 (s, COD-CH$_2$), 24.6 (s, CH$_3$-COO)

IR (KBr [cm$^{-1}$]) 3500, 3100, 2923, ν(CH); 2859, 2823, 1580, ν(CC), 1530, 1423, ν(CO), 1460, 1378, δ (CH$_3$), 1310, 1223, δ (N-Me), 1082, 1023, 956, 864, 743, 693, δ (CH-olefinic).

Structure

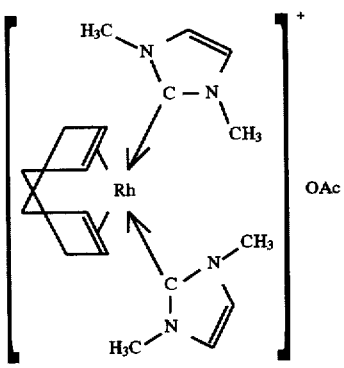

EXAMPLE 6

Chloro (η⁴-1,5-cyclooctadiene)-(1,3-dicyclohexylimidazolin-2-ylidene)-rhodium (I)

250 mg (0.51 mmol) of di(μ-chloro)bis(η⁴-1,5-cyclooctadiene)-dirhodium were dissolved in 20 ml of THF and admixed with 1 mmol of 1,3-dicyclohexylimidazolin-2-ylidene in THF by stirring at room temperature. The solvent was then stripped off in a high vacuum and the remaining residue was washed with 10 ml each of pentane and diethyl ether to obtain 410 mg (85%) of the desired product.

Characterization

¹H-NMR (400 MHz, CDCl₃, 20° C.) 6.78 (s, 2H, NCH), 4.94 (s, 2H, COD), 3.23 (s, 2H, COD), 4.17 (br, 2H, cyclohexyl), 2.4-1.2 (m, 28H, cyclohexyl, COD)

¹³C{1H}-NMR (CDCl₃, 100.1 MHz, 20° C.) 179.7 (d, ¹J(C-Rh)=50.0 Hz, carbene C), 117 (s, NCH), 97.4 (d, ¹J(C-Rh)=8 Hz, olefinic COD-CH), 67.2 (d, ¹J(C-Rh)=6 Hz, olefinic COD-CH), 60.0 (s, cyclo-hexyl-C), 34.4 (s, cyclohexyl-C), 33.6 (s, COD), 29.5 (s, COD), 24.1 (s, cyclohexyl-C), 25.2 (s, cyclohexyl-C)

Structure

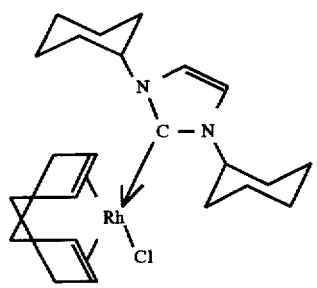

EXAMPLE 7

Dichloro (1,3-dimethylimidazolin-2-ylidene)-[η⁶-(1-isopropyl)-(4-methyl)-benzene]-ruthenium (II)

306 mg (0.5 mmol) of bis[μ-chloro)-chloro-{η⁶-(1-isopropyl)-(4-methyl)-benzene}-ruthenium (II)] were dissolved in 15 ml of THF and admixed at room temperature with 96 mg (1 mmol) (prepared according to 1a) of 1,3-dimethylimidazolin-2-ylidene in 5 ml of absolute THF. A deepening in the color from pale red to deep red indicated immediate conversion. After stirring for a further 15 minutes, the solvent was stripped off in a high vacuum. The residue was washed twice with 10 ml of ether and pentane each time. The product was taken in 10 ml of methylene chloride and carefully covered with 20 ml of pentane. This brought down deep red crystals, which were freed of the solvent mixture by decanting and drying in a high vacuum. The compound dissolved very readily in chloroform and methylene chloride, readily in toluene and THF to obtain 360 mg (90%) of the desired product.

Characterization

¹H-NMR (400 MHz, CDCl₃, 10° C., ppm) 6.97 (s, 2H) and 3.96 (s, 6H) (carbene) 5.36 (d, ³J=5.9 Hz, 2H), 5.10 (d, ³J=5.9 Hz, 2H), 2.04 (s, 3H, methyl), 1.21 (d, ³J=6.9 Hz, 6H, methyl), 2.88 (septet, ³J=6.9 Hz, 1H) (aromatic)

¹³C{¹H}-NMR (ppm) 123.71, 39.56 and 173.17 (carbene) 84.71, 82.20, 30.78, 22.46, 18.62 aromatic, plus two further peaks in the aromatics region (quaternary C)

MS (chemical ionization): m/z 400 (molecular peak, correct isotope pattern) 266 (M-C₁₀H₁₄) 231 (266 - Cl) 196 (231 - Cl) 134 (C₁₀H₁₄) 43 (134 - CH₃) 43 (propyl)

Structure

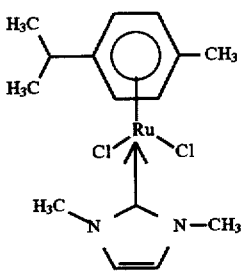

EXAMPLE 8

Dichlorobis[1-methyl-3-(ethyl-2-sulfonic acid, sodium salt)-imidazolin-2-ylidene]-platinum (II)

8a) Preparation of the ligand precursor: 1-methyl-3-(ethyl-2-sulfonic acid, sodium salt)-imidazolium bromide

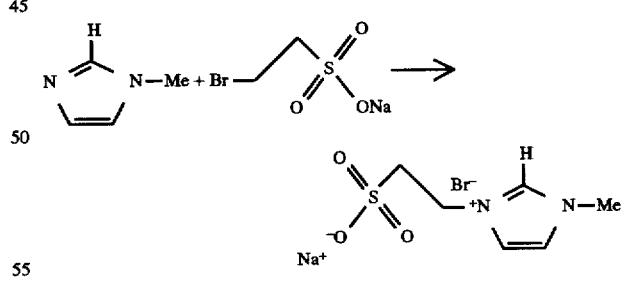

205 mg (2.5 mmol) of methylimidazole were stirred for three days at 70° C. with 210 mg (1 mmol) of sodium 2-bromomethanesulfonate without a solvent. After cooling, the residue was washed three times with 30 ml of diethyl ether to remove excess methylimidazole. Drying in a high vacuum (70° C., 10 hours) left a white solid which dissolved very readily in water, but hardly in organic solvents such as THF, toluene, pentane. The yield was 280 mg (96%) of the desired product.

Characterization

Analysis (calculated for $C_6H_{10}BrN_2NaO_3S$)

| calculated | % C 25.06 | % H 3.86 | % N 10.09 | % S 10.33 |
|---|---|---|---|---|
| observed | C 24.69 | H 3.40 | N 9.60 | S 10.90 |

$^1$H-NMR (400 MHz, $D_2O$, 20° C., ppm) 9.40 (s, 1H), 8.17 (d, 1H) 8.05 (d, 1H) (imidazole) 4.51 (s, 3H) (N-methyl) 5.22 (t, 2H, $^2J$=6.2 Hz), 4.05 (t, 2H, $^3J$=6.2 Hz ($CH_2$-$CH_2$)

$^{13}C\{^1H\}$-NMR 136.65, 123.55, 122.28, 35.66 carbene 49.78, 44.98 ($CH_2$-$CH_2$)

IR ($cm^{-1}$, KBr) 3156, 3108, 2964, 2927, 2851, 1638 (s) 1576, 1566, 1525, 1458, 1421, 1385, 1370, 1341 (w), 1279 (sh), 1206 (sst, br, SO), 1176 (sst), 1046, 744, 663, 620, 619, 575, 527

8b) Preparation of dichlorobis-[1-methyl-3-(ethyl-2-sulfonic acid, sodium salt)-imidazolin-2-ylidene]-platinum (II)

526 mg (2 mmol) of 1-methyl-3-(ethyl-2-sulfonic acid, sodium salt)-imidazolium bromide were stirred with 415 mg (1 mmol) of potassium tetrachloroplatinate (II) in 20 ml of degassed water at room temperature for 24 hours. The solution turned from dark red to yellowish orange. The solvent was distilled off under reduced pressure and the resulting residue was heated in a high vacuum at 215° C. for 5 hours to eliminate hydrogen chloride. The crude product was taken up in degassed water and column-chromatographed over Sephadex gel G 15. The yellowish orange compound was used without further purification.

EXAMPLE 9

Dichlorobis-[1-(ethyl-2-sulfonic acid, sodium salt)-3-(ethyl-2-sulfonic acid, potassium salt)-imidazolin-2-ylideneplatinum (II)

9a) Preparation of the ligand precursor: 1-(ethyl-2-sulfonic acid, sodium salt)-3-(ethyl-2-sulfonate)-imidazolium-betaine

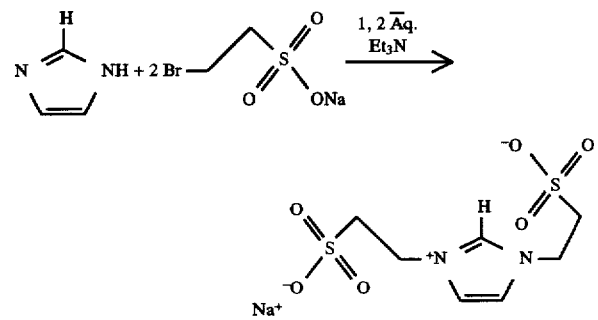

557 mg (8.2 mmol) of imidazole dissolved in 20 ml of dimethylacetamide were admixed with 1.5 ml (10.25 mmol) of triethylamine and 3.45 g (16.3 mmol) of sodium 2-bromoethane-sulfonate. On heating to 120° C., the original suspension cleared up and on further heating to 160° C., a white precipitate started to come down. To obtain complete conversion, the solution was refluxed for 4 hours and after cooling this solution to room temperature, the white precipitate was filtered off and washed 2 times with 20 ml each of ethanol and ether.

Characterization

Analysis (calculated for $C_7H_{11}N_2Na_1O_6S_2$)

| calculated | % C 27.40 | % H 3.62 | % N 9.14 | % S 20.94 |
|---|---|---|---|---|
| observed | C 26.85 | H 3.67 | N 8.82 | S 20.31 |

$^1$H-NMR (400 MHz, $D_2O$, 20° C., ppm) 9.18 (s, 1H), 7.55 (s, 2H) (imidazole) 4.58 (t, 4H, $^3J$=6.5 Hz), 3.40 (t, 4H, $^3J$=6.5 Hz), (2 times $CH_2$-$CH_2$)

$^{13}C\{^1H\}$-NMR 136.76, 122.59, carbene 49.77, 45.15 ($CH_2$-$CH_2$)

IR ($cm^{-1}$, KBr) 3152, 3104, 2992, 2978, 2954, 2930, 2851, 2677, 1641, 1564, 1459, 1410, 1367 (m) 1226-1197, (sst, br, u SO), 117 (sst), 1059 (sst), 1046 (sst), 900, 836, 746 (s), 641, 618, 590, 528

9b) Preparation of dichlorobis[1-(ethyl-2-sulfonic acid, sodium salt)-3-(ethyl-2-sulfonic acid, potassium salt)-imidazolin-2-ylidene]-platinum (II)

612 mg (2 mmol) of 1-(ethyl-2-sulfonic acid, sodium salt)-3-(ethyl-2-sulfonate)-imidazolium betaine were admixed with 415 mg (1 mmol) of potassium tetrachloroplatinate (II) in 20 ml of degassed water at room temperature for 24 hours. The solution turned from dark red to greenish yellow. The solvent was distilled off under reduced pressure and the resulting residue was heated in a high vacuum at 204° C. for 5 hours to eliminate hydrogen chloride. The crude product was taken up in degassed water and column-chromatographed over Sephadex gel G 15. The yellowish orange compound was used without further purification.

EXAMPLE 10

Dichlorobis[1-methyl-3-(butyl-4-sulfonic acid, potassium salt)-imidazolin-2-ylidene]-platinum (II)

10a) Preparation of the ligand precursor; 1-methyl-3-(butyl-4-sulfonate)-imidazolium betaine

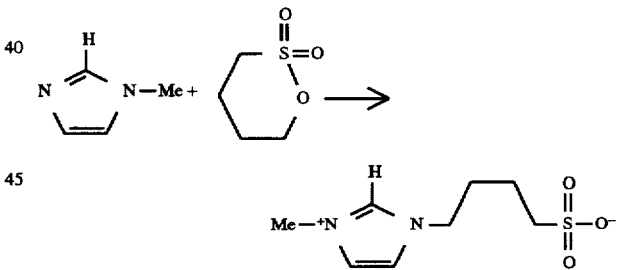

821 mg (10 mmol) of methylimidazole were stirred for 3 days at room temperature with 1361 mg (10 mmol) of 1,4-butanesultone without a solvent. After the substance had become solid, it was washed three times with 20 ml of toluene each time and dried in a high vacuum. The white solid dissolved readily in water, less readily in organic solvents. The yield was 2100 mg (96%) of the desired product.

Characterization

Analysis (calculated for $C_8H_{14}N_2O_3S$)

| calculated | % C 44.02 | % H 6.47 | % N 12.83 |
|---|---|---|---|
| observed | C 43.97 | H 6.33 | N 12.87 |

$^1$H-NMR (400 MHz, $D_2O$, 20° C., ppm) 8.65 (s, 1H), 7.41 (d, 1H, 3J=2.00 Hz), 7.34 (d, 1H, $^3J$=2.00 Hz) (imidazole)

3.62 (s, 3H) (N-methyl) 4.15 (m, 2H), 2.85 (m, 2H), 1.96 (m, 2H), 1.67 (m, 2H) ($CH_2$-$CH_2$-$CH_2$-$CH_2$)

$^{13}C\{^1H\}$-NMR 138.19, 123.61, 122.1 (imidazole) 35.75 (N-methyl) 50.28, 48.88, 36.48, 28.23, ($CH_2$-$CH_2$-$CH_2$-$CH_2$)

10b) Preparation of dichlorobis[1-(methyl-3-(butyl-4-sulfonic acid, potassium salt)-imidazolin-2-ylidene]-platinum (II)

376 mg (2 mmol) of 1-methyl-3-(butyl-4-sulfonate)-imidazolium betaine were admixed with 415 mg (1 mmol) of potassium tetrachloropalatinate (II) at room temperature for 24 hours. The solution turned from deep red to yellow. The solvent was distilled off under reduced pressure and the resulting residue was heated in a high vacuum at 195° C. for 5 hours to eliminate hydrogen chloride. The crude product was taken up in degassed water and column-chromatographed over Sephadex gel G 15. The yellow compound was used without further purification.

EXAMPLE 11

Diiodobis(1,3-dimethylimidazolin-2-ylidene)-palladium (II)

200 mg (0.89 mmol) of palladium (II) acetate were admixed in 25 ml of absolute THF at room temperature with 2.1 mole equivalents (420 mg, 1.87 mmol) of 1,3-dimethylimidazolium iodide. After refluxing for 30 minutes, the formerly dark brown solution turned yellow. The solvent was stripped off in a high vacuum and the residue was washed three times with 20 ml of absolute diethyl ether. Crystallization from 5 ml of methylene chloride and 3 ml of n-hexane yielded 370 mg of the desired complex as a yellow crystalline solid (yield: 75%).

Characterization

Analysis (calculated for $C_{10}H_{16}N_4I_2Pd$)

|  | % C | % H | % N |
|---|---|---|---|
| calculated | 21.73 | 2.92 | 10.14 |
| observed | C 23.26 | H 3.45 | N 10.00 |

(crystallized with $CH_2Cl_2$)

Decomposition point: 299° C.

$^1$H-NMR (400 MHz, $CDCl_3$, 20° C., ppm) δ H=3.92 (s, 12H, N-methyl), 7.24 (s, 4H, imidazole) $^{13}$C-NMR (100.53 MHz, $CDCl_3$, 20° C., ppm) δ C=168.18 (carbene C), 122.32 (imidazole), 38.22 (N-methyl)

The cis configuration of the complex was clearly confirmed by single-crystal X-ray structure analysis.

Structure

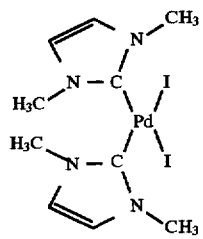

EXAMPLE 12

Diodo(1,1'-methylene-3,3'-dimethyldiimidazoline-2,2'-diylidene)-palladium (II)

Variant A 200 mg (0.89 mmol) of palladium (II) acetate were admixed in 10 ml of absolute toluene at 25° C. with 400 mg (0.89 mmol) of 1,1'-methylene-3,3'-dimethyldiimidazolium-diiodide. After refluxing for 2 hours, the solution, which had changed from dark red to yellow, was filtered with the aid of a cannula. The solvent was stripped off in a high vacuum and the residue was washed three times with 10 ml of absolute diethyl ether and 20 ml of absolute THF. The desired compound was obtained as a yellow solid (yield: 290 mg=61%).

Characterization

Analysis (calculated for $C_9H_{12}N_4I_2Pd$)

|  | % C | % H | % N | % I |
|---|---|---|---|---|
| calculated | 20.15 | 2.25 | 10.44 | 47.31 |
| observed | C 22.53 | H 2.78 | N 11.42 | I 47.6 |

(crystallized with THF)

$^1$H-NMR (400 MHz, $CDCl_3$, 20° C., ppm) δ H=3.92 (s, 6, N-methyl), 6.61 (s, 2H, $CH_2$), 7.41 and 7.43 (s, 4H, imidazole)

$^{13}$C-NMR (100.53 MHz, $CDCl_3$, 20° C., ppm) δ C=36.31 (N-methyl), 53.60 ($CH_2$), 121.87 and 124.35 (imidazole), 185.50 (carbene C)

Structure

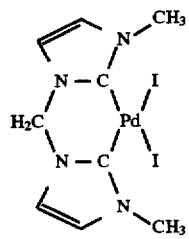

Variant B 1.26 g (4.5 mmol) of palladium (II) diiodide were suspended in 100 ml of n-hexane together with 4.80 g of 1,1'-methylene-3,3'-dimethyldiimidazolium diiodide. The fine suspension was cooled to dry ice temperature and admixed with 25 mmol of n-butyllithium as solution in n-hexane added dropwise with stirring. The solution of n-butyllithium should not be more concentrated than about 1 molar. After 2 hours of stirring at dry ice temperature, the solution was warmed to room temperature. In the meantime, an almost black precipitate was formed, which was isolated by removing the supernatant by means of a cannula. The precipitate was then extracted with methanol in a plurality of portions. The combined extracts which contain the desired compound were neutralized with dilute hydrochloric acid. After all volatiles had been removed in the vacuum of an oil pump, an almost colorless residue was obtained. The residue was crystallized from aqueous methanol to obtain 0.62 g of colorless crystals which decomposed at 215° to 216° C. while turning brown or black.

The same method affords the tetrafluoroborate (A=$BF_4$) starting from 1,1'-methylene-3,3'-dimethyldiimidazolium-bis-tetrafluoroborate.

EXAMPLE 13

Bis(1,3-dimethylimidazolin-2-ylidene)-palladium (II) diacetate 50 mg (0.22 mmol) of palladium (II) acetate were reacted in 20 ml of absolute toluene with 0.44 mmol of 1,3- dimethylimidazolin-2-ylidene (obtained by in situ formation from 1,3-dimethylimidazolium iodide with potassium tert-butoxide and sodium hydride in absolute THF) in 7.5 ml of absolute THF at room temperature. The resulting yellow precipitate was washed three times, crystallized from 3 ml of absolute methylene chloride and 2 ml of absolute n-hexane and dried in a high vacuum to obtain the desired product.

EXAMPLE 14

Dichlorobis (1,3-dimethylimidazolin-2-ylidene)-palladium (II)

190 mg (0.5 mmol) of bis(benzonitrile)-dichloropalladium (II) were dissolved in 15 ml of toluene and admixed with 1 mmol of free 1,3-dimethylimidazolin-2-ylidene dissolved in THF. Immediately on addition of the free carbene, the solution turned a lighter color, and as the reaction progressed, a precipitate was formed. The solvent was stripped in a high vacuum and the resulting pink solid was repeatedly washed with 10 ml of diethyl ether and 10 ml of pentane to obtain 148 mg (80%) of the desired product.

Characterization $^1$H- and $^{13}$C-NMR showed both the cis and the trans configuration in a ratio of about 1:1.

$^1$H-NMR (400 MHz, CD$_3$NO$_2$, 20° C., ppm) 7.11, 7.02 (s, in each case 2H, CH-CH), 4.07, 3.71 (s, in each case 6H, N-CH$_3$)

$^{13}$C{$^1$H}-NMR (100.1 MHz, CD$_3$NO$_2$, 20° C., ppm) 172.8, 171.4 (carbene C), 126.4, 125.6 (C=C), 40.4, 39.8 (N-CH$_3$)

IR (KBr, cm$^{-1}$) 1683, 1652 and 1635 (ν C=C), 1466 and 1397 (δ CH$_3$), 1230 (δ N-CH), 744 and 686 (γ CH=CH)

EXAMPLE 15

Dichlorobis(1,3-diisopropylimidazolin-2-ylidene)-platinum (II)

3.48 g (10 mmol) of cis-bis(acetonitrile)-platinum (II) chloride in 100 ml of acetonitrile were admixed with twice the molar amount of 1,3-diisopropylimidazolin-2-ylidene in THF solution at room temperature and stirred at 40° C. for 10 hours. The volatiles were then stripped off in the vacuum of an oil pump, and the colorless residue, which was insoluble in the customary organic solvents, was repeatedly washed with diethyl ether and finally dried in a high vacuum. The residue was thermally completely stable to above 200° C. and from the elemental analysis and also the NMR spectra corresponded to dichlorobis-(1,3-diisopropylimidazolin-2-ylidene)-platinum (II).

This compound was obtained by treating platinum (II) chloride first with 100 ml of acetonitrile or benzonitrile and then again reacting with twice the molar amount of carbene.

EXAMPLE 16

Chloro(η$^4$-1,5-cyclooctadiene)-(1,3-dimethylimidazolin-2-ylidene)-iridium (I)

282 mg (0.5 mmol) of di(μ-chloro)bis(η$^4$-1,5-cyclooctadiene)-diiridium were taken up at room temperature in 20 ml of absolute THF and admixed with 192 mg (1 mmol) of 1,3-dimethylimidazolin-2-ylidene. The immediate conversion was evident from the change in color from yellow to orange. Stirring was continued at room temperature for 30 minutes and the solvent was stripped off in a high vacuum. The residue was purified by washing with 10 ml of diethyl ether. The product was taken up in 10 ml of methylene chloride and carefully covered with 30 ml of pentane. The resulting yellow crystals were freed of the solvent mixture by decanting and drying in a high vacuum. The compound dissolved very readily in chloroform and methylene chloride, readily in THF and toluene, sparingly in diethyl ether and pentane with a yellow color. The yield of the desired product was 389 mg (90%).

Characterization $^1$H-NMR (400 MHz, CDCl$_3$, 20° C., ppm) 6.79 (s, 2H), 3.67 (s, 6H) (imidazole) 5.23 (m, 2H), 4.2 (m, 2H), 1.50 (m, 4H), 1.89 (m, 4H)

$^{13}$C{$^1$H}-NMR 37.77, 122.83, 176.62 (imidazole) 59.24, 83.64, 31.68, 31.06 (COD)

IR (KBr, cm$^{-1}$) 3500, 3158, 3104, ν(CH), 2919, 2876, 2828, 1652, 1575, ν(CC), 1456, 1386, δ (CH$_3$), 1324, 1229, δ (N-Me), 1115, 1081, 997, 872, 803, 745, 700, δ (CH olefinic), 466

MS (chemical ionization): m/z 432 (molecular peak, correct isotope pattern) 397 (M - Cl, correct isotope pattern)

EXAMPLE 17

Tricarbonyldichloro(1,3-dimethylimidazolin-2-ylidene)-osmium (II)

1 mmol of 1,3-dimethylimidazolin-2-ylidene dissolved in 5 ml of anhydrous THF was added dropwise to a thoroughly stirred solution of 345 mg (0.5 mmol) of bis[(μ-chloro) chlorotricarbonyl-osmium (II)] in 15 ml of anhydrous THF. After the volatiles had been stripped off in a high vacuum, the residue was washed with ether (2×20 ml) and pentane (2×20 ml) and dried in a high vacuum. The product was virtually insoluble even in methylene chloride. Crystals suitable for an X-ray structure analysis were obtained by slowly evaporating nitromethane from a very concentrated solution at room temperature into the laboratory atmosphere. The yield of the desired product was 418 mg (95%).

Characterization $^1$H-NMR (400 MHz, CD$_3$NO$_2$, 20° C., ppm): δ=7.23 (s, 2H) 4.14 (s, 6H) (carbene)

$^{13}$C{$^1$H}-NMR (100.1 MHz, CD$_3$NO$_2$, 20° C., ppm): δ=171.54 (carbene C), 168.94, 168.49 (CO), 125.70 (NCH), 40.30 (NCH$_3$)

IR (KBr, cm$^{-1}$): 2115 (s, ν(CO)), 2014 (ss, ν(CO)), 1932 (s, ν (CO))

MS (chemical ionization): m/z 442 (molecular peak, correct isotope pattern) 407 (M - Cl, correct isotope pattern) 379 (407 - CO, correct isotope pattern)

Structure

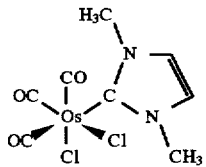

Various modifications of the complexes of the invention may be made without departing from the spirit or scope thereof and it is to be understood that the invention is intended to be limited only as defined in the appended claims.

What we claim is:

1. A metal complex of the formula $[L_aM_bX_c]^r(A)_n$     I wherein M is ion of oxidation state of 1 to 8 of metals of groups 8, 9 and 10 of the periodic table as central atom, X is uni- or multidentate charged or uncharged ligands bound to the central atom, and L are ligands similarly bound to the central atom M, selected from the group consisting of monocarbenes of the formulae

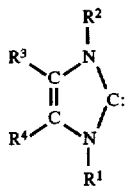   II and

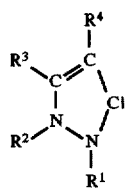   III or dicarbenes of the formulae

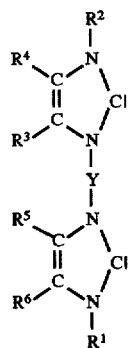   IV and

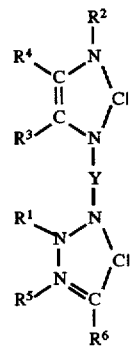   V wherein $R^1$, $R^2$, $R^3$, $R^4$, $R^5$ and $R^6$ are individually selected from the group consisting of optionally sulfonated alkyl of 1 to 7 carbon atoms, optionally sulfonated aliphatic mono- or poly-cyclics of 5 to 18 carbon atoms, optionally sulfonated alkenyl of 2 to 5 carbon atoms, optionally sulfonated aryl of 6 to 14 carbon atoms and optionally sulfonated arylalkyl of 7 to 19 carbon atoms, or $R^3$, $R^4$, $R^5$ and $R^6$ also can be hydrogen, or $R^3$ and $R^4$ together and $R^5$ and $R^6$ together in each case with the carbon atoms to which they are attached individually form fused and optionally sulfonated groups of 3 to 7 carbon atoms, Y is an optionally unsaturated alkylidene of 1 to 4 carbon atoms or a dialkyl-silylene or a tetraalkyldisilylene, A is a singly charged anion or the chemical equivalent of a multiply charged anion, b is an integer from 1 to 3, a is an integer from 1 to 5×b and c=0 or an integer from 1 to 4×b, n=0 or an integer from 1 to 6, and c+n>0, but not (N,N'-dimethyl-benzimidazolin-2-ylidene)-chloro-(1,5-cyclooctadiene)-rhodium.

2. A metal complex of claim 1 wherein X in formula I is selected from the group consisting of hydrogen, hydrogen ion, halogen, halogen ions, pseudohalides, carboxylate ions, sulfonate ions, amide, alkyl of 1 to 7 carbon atoms, alcoholates, acetylacetonate, carbon monoxide, nitrogen monoxide, nitriles, isonitriles, mono- and diolefins, alkynes and π-aromatics.

3. A metal complex of claim 1 wherein, in the formulae II, III, IV and V, $R^1$, $R^2$, $R^3$, $R^4$, $R^5$ and $R^6$ are individually selected from the group consisting of methyl, isopropyl, tert-butyl, benzyl, triphenylmethyl, phenyl, tolyl, xylyl and mesityl.

4. A metal complex of claim 1 wherein in formulae II, III, IV and V, $R^1$ and $R^2$ are individually selected from the group consisting of methyl, tert-butyl, phenyl, benzyl and o-tolyl.

5. A metal complex of claim 1 wherein in the formulae II, III, IV and V, $R^3$ and $R^4$ are each hydrogen or methyl.

6. A metal complex of claim 1 wherein, the formulae II, III, IV and V, $R^3$ and $R^4$ together and $R^5$ and $R^6$ together form $(CH)_4$, $(CH_2)_4$ and/or $(CH_2)_5$.

7. A metal complex of claim 1 wherein, in the formulae IV and V, Y is selected from the group consisting of methylene, dimethylene, diphenylmethylene and ethylidene.

8. A metal complex of claim 1 wherein, in the formulae IV and V, Y is dimethylsilylene or tetramethyldisilylene.

9. A metal complex of claim 1 wherein, in formula I, a is 1 or 2.

10. A metal complex of claim 1 wherein, in formula I, b is 1.

11. A metal complex of claim 1 wherein, in formula I, n is from 0 to 3.

12. A metal complex of claim 1 wherein, in formula I, A is selected from the group consisting of halide and pseudohalide ions, the tetraphenylborate, tetrafluoroborate, hexafluorophosphate, acetate, tetracarbonylcobaltate, hexafluoroferrate, tetrachloroferrate, tetrachloroaluminate and tetrachloropalladate ion.

* * * * *